(12) United States Patent
Inoue et al.

(10) Patent No.: US 10,100,295 B2
(45) Date of Patent: Oct. 16, 2018

(54) MODIFIED XYLANASE (71) Applicant: National Institute of Advanced Industrial Science and Technology, Tokyo (JP)

(72) Inventors: Hiroyuki Inoue, Hiroshima (JP); Tatsuya Fujii, Hiroshima (JP); Kazuhiko Ishikawa, Osaka (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 15/565,463

(22) PCT Filed: Apr. 12, 2016

(86) PCT No.: PCT/JP2016/061759
§ 371 (c)(1),
(2) Date: Oct. 10, 2017

(87) PCT Pub. No.: WO2016/167235
PCT Pub. Date: Oct. 20, 2016

(65) Prior Publication Data
US 2018/0080015 A1 Mar. 22, 2018

(30) Foreign Application Priority Data
Apr. 14, 2015 (JP) .................................. 2015-082133

(51) Int. Cl.
*C12N 9/26* (2006.01)
*C12N 9/24* (2006.01)

(52) U.S. Cl.
CPC .................................. *C12N 9/2482* (2013.01)

(58) Field of Classification Search
CPC .................... C12N 15/8246; C12Y 302/01008
USPC .................... 435/201, 419; 536/23.2, 24.5
See application file for complete search history.

(56) References Cited

U.S. PATENT DOCUMENTS

| 8,211,665 B2 * | 7/2012 | Tang ................... C12N 15/8246 435/41 |
| 2011/0078830 A1 * | 3/2011 | Tang ................... C12N 15/8246 800/298 |
| 2015/0284699 A1 | 10/2015 | Ishikawa et al. |

FOREIGN PATENT DOCUMENTS

| JP | H06-261750 | 9/1994 |
| WO | WO 96/02632 | 2/1996 |
| WO | WO 2014/061763 | 4/2014 |

OTHER PUBLICATIONS

Ali, et al., "Importance of the Carbohydrate-Binding Module of *Clostridium stercorarium* Xyn10B to Xylan Hydrolysis", Biosci. Biotechnol. Biochem., 65, (1), 41-47, 2001.
Black, et al., "A modular xylanase containing a novel non-catalytic xylan-specific binding domain", Biochem J (1995) 307, 191-195.
Black, et al., "Cellulose binding domains and linker sequences potentiate the activity of hemicellulases against complex substrates" Journal of Biotechnology, 57 (1997) 59-69.
De La Mare, et al., "Molecular and biochemical characterization of three GH62 α-L-arabinofuranosidases from the soil deuteromycete *Penicillium funiculosum*", Enzyme and Microbial Technology 53 (2013) 351-358.
Inoue, et al., "Contribution of a family 1 carbohydrate-binding module in thermostable glycodise hydrolase 10 xylanase from Talaromyces cellylolticus toward synergistic enzymatic hydrolysis of lignocellulose", Biotechnology for Biofuels (2015) 8:77.
Kishishita, et al., "Cellulose-inducible xylanase Xyl10A from Acremonium cellulolyticus:Purification, cloning and homologous expression", Protein Expression and Purification 94 (2014) 40-45.
Sermsathanaswadi, et al., "The C-terminal region of xylanase domain in Xyn11A from *Paenibacillys curdlanolyticus* B-6 plays an important role in structural stability", Appl Microbio Biotechnol (2014) 98:8223-8233.

* cited by examiner

*Primary Examiner* — Tekchand Saidha
(74) *Attorney, Agent, or Firm* — Cesari and McKenna, LLP (57) ABSTRACT

Provided is a modified xylanase. The polypeptide has xylanase activity and has an amino acid sequence with deletion of at least 12 consecutive amino acid residues at the C-terminus of the amino acid sequence of SEQ ID NO: 1 or an amino acid sequence having at least 90% identity with the amino acid sequence of SEQ ID NO: 1.

22 Claims, 2 Drawing Sheets
Specification includes a Sequence Listing.

MODIFIED XYLANASE

CROSS REFERENCE TO RELATED APPLICATIONS

This application is the National Stage of International Application No. PCT/JP2016/061759, filed on Apr. 12, 2016, which claims priority to Japanese Application No. 2015-082133, filed on Apr. 14, 2015. The contents of both applications are hereby incorporated by reference in their entirety.

TECHNICAL FIELD

A modified xylanase and its related techniques are disclosed.

BACKGROUND ART

Xylan is one of the ubiquitous, naturally occurring polysaccharides, and is a major constituent of plants. From a structural viewpoint, xylan is a macromolecular polysaccharide containing a main chain made from units of xylose, which is polymerized by β-1,4 xyloside linkage. Xylan is present in nature as a homoxylan consisting of only xylose, and as a heteroxylan such as arabinoxylan having a structure in which arabinose is branched from the main chain.

Xylanase is a generic term for a group of enzymes that hydrolyze xylan, and that are widely found in animals, plants, and microorganisms. There has been research largely focusing on xylanase derived from bacteria, actinomycetes, yeast, fungi, and the like. Xylanase is used in the production of xylooligosaccharides or xylose from xylan, as well as in biomass processing. In particular, xylanase has recently been brought to attention as being useful from the point of view of enzyme utilization in plant biomass processing, such as lignocellulose. For example, xylanase is used in the enzymatic degradation of agricultural waste for alcohol fuels, enzymatic treatment for liberating saccharides in animal feed, enzymatic treatment for dissolving pulp in the step of obtaining cellulose, and enzymatic treatment for bleaching wood pulp. Xylanase is also used in animal feed and in the food-processing field (JPH06-261750A).

*Talaromyces* (former name: *Acremonium*) *cellulolyticus* CF-2612 strain is reported to produce a high level of xylanase (hereinafter "Xyl10A") upon induction by cellulose (NPL 1).

CITATION LIST

Patent Literature

PTL 1: JPH06-261750A

Non-Patent Literature

NPL 1: Protein. Expr. Purif. 94: 40-45 (2014)
NPL 2: Journal of Biotechnology, 57 (1997), 59-69
NPL 3: Biosci. Biotechnol. Biochem. 65 (1), 41-47, 2001
NPL 4: Biochem. J. (1995), 307, 191-195
NPL 5: Enzyme Microb. Technol. 2013, 53 (5): 351-358

SUMMARY OF INVENTION

Technical Problem

An object of the present invention is to provide xylanase with more improved characteristics.

Solution to Problem

It has been reported that removal of the cellulose-binding domain (or module) of xylanase causes a reduction in the xylanase activity (NPL 2 and NPL 3), or has no significant influence on the enzyme activity (NPL 4). Further, for glucosyl hydrolases other than xylanase, it has also been reported that removal of the cellulose-binding domain (or module) leads to a reduction in the enzyme activity (NPL 5). However, it was found that when the cellulose-binding module 1 (CBM1) of xylanase (Xyl10A) produced by *Talaromyces cellulolyticus* CF-2612 strain was deleted, the enzyme activity as xylanase was significantly increased. Based upon this finding, further studies were conducted. Thus, inventions shown in the following are provided.

Item 1.
A polypeptide having xylanase activity and having an amino acid sequence with deletion of at least 12 consecutive amino acid residues at the C-terminus of the amino acid sequence of SEQ ID NO: 1 or an amino acid sequence having at least 90% identity with the amino acid sequence of SEQ ID NO: 1.

Item 2.
The polypeptide according to Item 1, wherein the at least 12 amino acid residues are 12 or more amino acid residues and 73 or less amino acid residues.

Item 3.
The polypeptide according to Item 1 or 2, wherein the polypeptide is stable at 70° C.

Item 4.
A polynucleotide encoding the polypeptide according to any one of claims 1 to 3.

Item 5.
An expression vector incorporating the polynucleotide according to Item 4.

Item 6.
A host cell containing the polynucleotide according to Item 4 and/or the expression vector according to Item 5.

Item 7.
A process for producing the polypeptide according to any one of Items 1 to 3, the process comprising:
culturing the host cell according to Item 6; and
collecting the polypeptide according to any one of Items 1 to 3.

Advantageous Effects of Invention

A modified xylanase in which the enzyme activity and/or other characteristics are modified is provided.

DESCRIPTION OF EMBODIMENTS

1. Polypeptide

The polypeptide having xylanase activity preferably has an amino acid sequence with deletion of at least 12 consecutive amino acid residues at the C-terminus of the amino acid sequence of SEQ ID NO: 1 or an amino acid sequence having at least 80% identity with the amino acid sequence of SEQ ID NO: 1.

The amino acid sequence of SEQ ID NO: 1 is the amino acid sequence of xylanase (Xyl10A) produced by *Talaromyces cellulolyticus* CF-2612 strain. The region at positions 1 to 316 of the amino acid sequence of SEQ ID NO: 1 is considered to correspond to the catalytic domain of xylanase (Xyl10A), the region at positions 317 to 353 is considered to correspond to the linker sequence, and the region at positions 354 to 388 is considered to correspond to the cellulose-binding module (CBM).

Therefore, the 12 consecutive amino acids at the C-terminus of the amino acid sequence of SEQ ID NO: 1 correspond to part of the CBM of xylanase (Xyl10A). The "at least 12 consecutive amino acid residues" are preferably 12 or more consecutive amino acid residues and 73 or fewer consecutive amino acid residues. The region comprising 73 consecutive amino acid residues at the C-terminus of the amino acid sequence of SEQ ID NO: 1 includes the entire region of the CBM and linker sequence of xylanase (Xyl10A).

In one embodiment, the number of amino acid residues deleted is not particularly limited and can be suitably selected, as long as certain characteristics are modified from wild-type xylanase (Xyl10A). For example, the number of amino acid residues deleted may be 1 or more, 2 or more, 3 or more, 4 or more, 5 or more, 6 or more, 7 or more, 8 or more, 9 or more, 10 or more, 11 or more, 12 or more, 15 or more, 20 or more, 25 or more, 30 or more, 35 or more, 40 or more, 45 or more, 50 or more, 55 or more, 60 or more, 65 or more, or 70 or more amino acids at the C-terminus of the amino acid sequence of SEQ ID NO: 1 or an amino acid sequence having at least 80% identity therewith; and may be 73 or fewer, 70 or fewer, 65 or fewer, 60 or fewer, 55 or fewer, 50 or fewer, 45 or fewer, 40 or fewer, 35 or fewer, 30 or fewer, 25 or fewer, 20 or fewer, 15 or fewer, 10 or fewer, or 5 or fewer amino acids.

The identity is preferably at least 85%, preferably at least 90%, preferably at least 95%, preferably at least 96%, preferably at least 97%, preferably at least 98%, or preferably at least 99%. Specific examples of the amino acid sequence having an identity of above a certain level with the amino acid sequence of SEQ ID NO: 1 include the amino acid sequence of SEQ ID NO: 7. The amino acid sequence of SEQ ID NO: 7 is the amino acid sequence of xylanase (XynD) derived from *Penicillium funiculosum*. The identity of the amino acid sequence of SEQ ID NO: 7 with the amino acid sequence of SEQ ID NO: 1 is 97%.

The amino acid sequence identity can be determined by using a commercially available analytical tool or an analytical tool available through telecommunication lines (Internet). For example, the amino acid sequence identity can be determined by using ClustalW Ver. 2.1 Pairwise Alignment (http://clustalw.ddbj.nig.ac.jp/index.php?lang=ja) with default parameters. Alternatively, the amino acid sequence identity can be determined by using the BLAST (Basic Local Alignment Search Tool) homology algorithm available from the National Center for Biotechnology Information (NCBI) at http://www.ncbi.nlm.nih.gov/BLAST/ with default parameters (default setting).

In the amino acid sequence having an identity of above a certain level with the amino acid sequence of SEQ ID NO: 1, it is preferable that 10% or more, preferably 20% or more, preferably 30% or more, preferably 40% or more, preferably 50% or more, preferably 60% or more, preferably 70% or more, preferably 80% or more, preferably 90% or more, or preferably 95% or more, of amino acid residues different from the amino acid sequence of SEQ ID NO: 1 be conservatively substituted amino acid residues. The term "conservatively substituted amino acid residues" refers to amino acid residues that have a side chain of nature similar to that of amino acid residues to be substituted.

For example, amino acid residues can be classified into families of similar nature according to their side chains, such as basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). The term "conservative amino acid substitution" refers to substitution of amino acid residues with other amino acid residues belonging to the same family as the amino acid residues to be substituted.

In one embodiment, the amino acid sequence having an identity of above a certain level with the amino acid sequence of SEQ ID NO: 1 includes amino acid sequences with substitution, deletion, insertion and/or addition of one or more amino acids in the amino acid sequence of SEQ ID NO: 1.

The glutamic acid residue at position 129 and the glutamic acid residue at position 236 in the amino acid sequence of SEQ ID NO: 1 are considered to constitute the active center. The lysine residue at position 47, the histidine residue at position 80, the tryptophan residue at position 84, the glutamine residue at position 204, the histidine residue at position 206, the tryptophan residue at position 276, and the tryptophan residue at position 284 are considered to be involved in the interaction with substrates. Therefore, it is preferable that these amino acid residues be also conserved in the amino acid sequence having an identity of above a certain level with SEQ ID NO: 1. In one embodiment, it is preferable that 3 amino acid residues, 2 amino acid residue, or 1 amino acid residue, before and after these amino acid residues be also conserved.

In the polypeptide having xylanase activity, any sequence may be added to the N-terminal side of the amino acid sequence of SEQ ID NO: 1 or an amino acid sequence having an identity of above a certain level with SEQ ID NO: 1, as long as certain characteristics are modified from wild-type xylanase (Xyl10A). The number of amino acid residues to be added is not particularly limited. For example, the number of amino acid residues to be added is 1 or more, 2 or more, 3 or more, 4 or more, 5 or more, 6 or more, 7 or more, 8 or more, 9 or more, 10 or more, 11 or more, 12 or more, 15 or more, 20 or more, 25 or more, 30 or more, 35 or more, 40 or more, 45 or more, 50 or more, 55 or more, or 60 or more. The number of amino acid residues to be added is, for example, 80 or fewer, 75 or fewer, 70 or fewer, 65 or fewer, 60 or fewer, 55 or fewer, 50 or fewer, 45 or fewer, 40 or fewer, 35 or fewer, 30 or fewer, 25 or fewer, 20 or fewer, 15 or fewer, 10 or fewer, or 5 or fewer.

Figure 3:
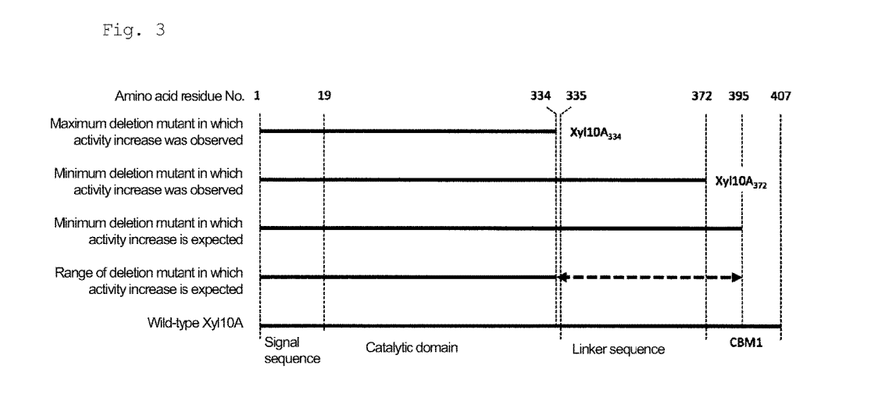
FIG. 3 shows the structure of the modified xylanases produced in the Examples, and the structure of other modified xylanases assumed from the produced modified xylanases.

It is preferable that the amino acid residues added to the above N-terminal side constitute a signal peptide. The specific amino acid sequence of the signal peptide may be any amino acid sequence, as long as it functions as a signal peptide, and it can be suitably designed depending on the intended use, the type of host cell, etc. For example, the signal peptide is the same amino acid sequence as the signal peptide of wild-type xylanase (Xyl10A) or an amino acid sequence having at least 85% identity therewith. The "identity" herein is preferably at least 90%, preferably at least 95%, preferably at least 96%, preferably at least 97%, preferably at least 98%, or preferably at least 99%. The signal peptide of wild-type xylanase (Xyl10A) has the amino acid sequence of SEQ ID NO: 2. An amino acid sequence in which the amino acid sequence of SEQ ID NO: 2 is attached to the N-terminus of the amino acid sequence of SEQ ID NO: 1 is the amino acid sequence of SEQ ID NO: 3. The structure of xylanase shown in FIG. 3 is based on the amino acid sequence of SEQ ID NO: 3 (i.e., a primary structure having a signal peptide).

In addition to a signal peptide, for example, a tag useful for polypeptide purification and/or a sequence that forms a useful domain structure (e.g., cellulose-binding CBM2a, CBM3, CBM5, CBM10, etc., and xylan-binding CBM2b, CBM6, CBM9, and CBM22) may be added to the N-terminus, C-terminus, or both terminuses of the polypeptide having xylanase activity. Such tags are known in the art, and can be suitably selected for use. The sequence to be added is any sequence, as long as the xylanase activity is maintained.

It is preferable that the polypeptide having xylanase activity have higher enzyme activity as xylanase (i.e., xylanase activity) than that of wild-type xylanase (Xyl10A). The xylanase activity is measured under the following conditions. An enzyme protein (final concentration: 0.0005 to 0.001 mg/ml) is added to a 50-mM sodium acetate buffer (pH 5.0) containing birchwood xylan (final concentration: 1%) as a substrate to initiate the reaction, and the mixture is kept warm at 45° C. for 10 minutes. Reducing sugars produced during the reaction are quantified by the DNS method using 3,5-dinitrosalicylic acid as a color developer (Methods in Enzymology 160: 87-176 (1988)) according to an ordinary technique. The amount of reducing sugars is quantified by a calibration curve using xylose as a standard sugar. For the enzyme activity, the enzyme level that produces 1 µmol of reducing sugar per minute is defined as 1 U.

In one embodiment, the xylanase activity of the polypeptide having xylanase activity is preferably 1.3 times higher or more, preferably 1.5 times higher or more, preferably 1.6 times higher or more, preferably 1.7 times higher or more, preferably 1.8 times higher or more, preferably 1.9 times higher or more, preferably 2 times higher or more, preferably 2.5 times higher or more, preferably 3 times higher or more, preferably 3.5 times higher or more, or preferably 4 times higher or more than the activity of wild-type xylanase.

It is preferable that the polypeptide having xylanase activity have temperature stability equal to or higher than that of wild-type xylanase (Xyl10A). For example, the peptide having xylanase activity is preferably stable at 70° C. The phrase "stable at 70° C." used herein means that the enzyme activity is not substantially reduced even when the polypeptide is maintained in a 50 mM sodium acetate buffer (pH 5.0) at 70° C. for 10 minutes. The phrase "the enzyme activity is not substantially reduced" means that, for example, enzyme activity is not reduced 15% or more from that before the above treatment.

It is preferable that the polypeptide having xylanase activity have pH stability equal to or higher than that of wild-type xylanase (Xyl10A). It is preferable that the polypeptide having xylanase activity have an optimal active pH of 4 to 5.

The polypeptide can be produced in accordance with a genetic engineering procedure by using the later-described polynucleotide. The polypeptide can also be produced on the basis of the information of the amino acid sequences of SEQ ID NOs: 1 to 3 by using an ordinary protein chemical synthesis technique (e.g., liquid-phase method and solid-phase method).

The polypeptide may be present in any state. For example, the polypeptide can be an isolated polypeptide, a purified polypeptide, a roughly purified polypeptide, a polypeptide present in a culture medium, a polypeptide present in a buffer suitable for maintaining the enzyme activity, a freeze-dried polypeptide, a polypeptide stored in a solution containing a preservative or a stabilizer, such as glycerol, a spray-dried polypeptide, or the like. In one embodiment, the polypeptide is preferably a freeze-dried purified polypeptide, a purified polypeptide stored in a solution containing a preservative or a stabilizer, such as glycerol, or a spray-dried purified polypeptide.

2. Polynucleotide

A polynucleotide encoding the polypeptide having xylanase activity described above has any base sequence without particular limitation. For example, the base sequence of the polynucleotide is any one of the base sequences of SEQ ID NOs: 4 to 6, or a base sequence having at least 80% identity with these base sequences. The identity herein is preferably at least 85%, preferably at least 90%, preferably at least 95%, preferably at least 96%, preferably at least 97%, preferably at least 98%, or preferably at least 99%.

The base sequence of SEQ ID NO: 4 is an example of base sequences that encode the amino acid sequence of SEQ ID NO: 1. The base sequence of SEQ ID NO: 5 is an example of base sequences that encode the amino acid sequence of SEQ ID NO: 3 (i.e., polypeptide having a signal peptide). It is preferable that the polynucleotide encode a polypeptide containing a signal peptide. Therefore, it is preferable that the polynucleotide have SEQ ID NO: 5 or a base sequence having an identity of above a certain level with the SEQ ID NO: 5. The polynucleotide encoding the above polypeptide also includes polynucleotides containing any introns. The base sequence of SEQ ID NO: 6 is an example of such polynucleotides. In the base sequence of SEQ ID NO: 6, the regions at positions 199 to 252, 386 to 458, and 573 to 666 are introns.

The base sequence identity can be determined by using a commercially available analytical tool or an analytical tool available through telecommunication lines (Internet). For example, software such as FASTA, BLAST, PSI-BLAST, or SSEARCH can be used to determine the identity. The major initial conditions typically applied to a BLAST search are specifically as follows. In Advanced BLAST 2.1, a blastn program is used, and the parameters are set to default values to perform a search. The homology value (%) of a nucleotide sequence is then calculated.

The polynucleotide encoding the polypeptide having xylanase activity described above may be a polynucleotide that hybridizes with a polynucleotide complementary to a polynucleotide having the base sequence of SEQ ID NO: 4 or 5 under stringent conditions. The term "stringent conditions" refers to the conditions in which a "specific" hybrid is formed, and a "non-specific" hybrid is not formed. Specific examples of stringent conditions include: hybridization at 42° C. and washing at 42° C. with a buffer containing 1×SSC and 0.1% SDS; preferably hybridization at 65° C. and washing at 65° C. with a buffer containing 0.1×SSC and 0.1% SDS. Besides the temperature conditions, a variety of parameters that affect the stringency of hybridization are known, and one of ordinary skill in the art can suitably combine the parameters to design stringency equivalent to the above-described stringency of hybridization.

Polynucleotides that hybridize with a polynucleotide having a base sequence complementary to the base sequence of SEQ ID NO: 4 or 5 under stringent conditions include those having a stop codon in their sequences, and those having a mutation in the active center and encoding polypeptides that do not have desired activity. However, such polypeptides can be avoided by using site-specific mutagenesis, or can be easily removed by measuring the enzyme activity with a known technique.

The polynucleotide is preferably an isolated polynucleotide. The term "isolated polynucleotide" means that the polynucleotide is separated from components such as other nucleic acids and proteins that naturally accompany it. However, the polynucleotide may contain a portion of other nucleic acid components, such as nucleic acid sequences that naturally flank the polynucleotide sequence (e.g., the promoter region sequence and terminator sequence). Polynucleotides prepared by a genetic engineering procedure, such as cDNA molecules, are preferably substantially free of other components such as cell components and culture media. Likewise, polynucleotides prepared by chemical synthesis are preferably substantially free of precursors (starting materials) such as dNTP, as well as substances, etc., used in the synthetic process.

The polynucleotide can easily be prepared on the basis of the base sequences of SEQ ID NOs: 4 to 6 by using a chemical DNA synthesis technique (e.g., phosphoramidite method) or a genetic engineering technique.

3. Expression Vector

It is preferable that the expression vector be a recombinant vector incorporating the above polynucleotide in an expressible state in a suitable host. The structure of the expression vector is not particularly limited as long as the above polynucleotide is incorporated in an expressible state, and the expression vector may further comprise polynucleotides that encode other proteins.

The type of vector can be suitably selected according to the type of host cell. Examples of vectors include plasmid vectors, cosmid vectors, phage vectors, and virus vectors (e.g., adenovirus vectors, retroviral vectors, and herpes viral vectors).

Examples of vectors that enable expression in *Escherichia coli* include pUC19, pUC18, pBR322, pHSG299, pHSG298, pHSG399, pHSG398, RSF1010, pMW119, pMW118, pMW219, pMW218, and pET. Examples of vectors that enable expression in yeast include pBR322, pJDB207, pSH15, pSH19, pYepSec1, pMFa, and pYES2. Examples of vectors that enable expression in insects include pAc and pVL. Examples of vectors that enable expression in *Talaromyces cellulolyticus* by self-cloning include pANC202 (J. Ind. Microbilol. Biotechnol. 40: 823-830 (2013)), pbs-pyrF (Biosci. Biotecnol. Biochem. 76: 245-249 (2012)), and pCBHEX/DtR2 (JP4257759B).

For a eukaryotic host cell, suitably used expression vectors are those comprising, upstream of the polynucleotide to be expressed, a promoter, an RNA splicing site, a polyadenylation site, a transcription termination sequence, and the like. The expression vectors may further optionally comprise a replication origin, an enhancer, and/or a selection marker.

4. Transformant

It is preferable that the transformant be obtained by transformation with the above-described recombinant vector. The host cell used in transformation is not particularly limited as long as the above polypeptide can be produced, and either prokaryotic cells or eukaryotic cells can be used. Examples of host cells include prokaryotic cells including bacteria of genus *Escherichia coli* (e.g., HB101, MC1061, JM109, CJ236, and MV1184), coryneform bacteria such as *Corynebacterium glutamicum*, actinomycetes such as bacteria of genus *Streptomyces*, bacteria of genus *Bacillus* such as *Bacillus subtilis*, bacteria of genus *Streptococcus*, and bacteria of genus *Staphylococcus*; yeast such as genus *Saccharomyces*, genus *Pichia*, and genus *Kluyveromyces*, and fungal cells such as genus *Aspergillus*, genus *Penicillium*, genus *Trichoderma*, genus *Acremonium*, and genus *Talaromyces*; insect cells including *Drosophila* S2, *Spodoptera* Sf9, and silkworm-culturing cells; and plant cells. In one embodiment, it is preferable to use *Bacillus subtilis*, yeast, *Aspergillus oryzae*, actinomycetes, or the like as a host, because they secrete polypeptides outside the cells (microbial cells).

To introduce the recombinant expression vector into a host cell, a conventional method can be used. Examples include a variety of methods, such as the competent cell method, the protoplast method, the electroporation method, the microinjection method, and the liposome fusion method. Transformation can be performed by a method suitably selected from these methods.

The transformant can be used to produce the polypeptide mentioned above.

5. Process for Producing Polypeptide Using Transformant

The above polypeptide can be produced by culturing the above transformant, and collecting the polypeptide having xylanase activity from the culture. The culture can be carried out by suitably selecting a culture medium suitable for the host. The culture can be carried out, for example, until a sufficient amount of the polypeptide is produced, with monitoring of the activity of the polypeptide produced inside and outside of the transformant as a guide.

The culture medium may be suitably selected from conventionally used media according to the host cell. The culture can be carried out under conditions suitable for growth of the host cell. Examples of media used for culturing *Escherichia coli* include nutrient media such as LB medium, and minimal media to which a carbon source, a nitrogen source, a vitamin source, and the like are added, such as M9 medium.

The culture conditions can also be suitably determined according to the type of host. For example, the culture can be carried out at 16 to 42° C., preferably 25 to 37° C., for 5 to 168 hours, preferably for 8 to 96 hours. Either shaking culture or static culture may be selected according to the type of host. The medium may optionally be agitated, and ventilation may optionally be provided. When an induction promoter is used for expressing xylanase, a promoter-inducing agent may be added to the medium to perform a culture.

Purification or isolation of xylanase from a culture supernatant can be carried out by suitably combining known techniques. Examples of techniques for use include ammonium sulfate precipitation, solvent precipitation (e.g., ethanol), dialysis, ultrafiltration, acid extraction, and a variety of chromatographic approaches (e.g., gel filtration chromatography, anion- or cation-exchange chromatography, phosphocellulose chromatography, hydrophobic interaction chromatography, affinity chromatography, hydroxyapatite chromatography, lectin chromatography, and high-performance liquid chromatography). Examples of carriers used in affinity chromatography include carriers to which an antibody against xylanase is bound, and carriers to which a substance with affinity for a peptide tag is bound, when the peptide tag is added to xylanase.

When the polypeptide is accumulated inside the host cells, the transformed cells are disrupted, and xylanase is purified or isolated from the centrifuged supernatant of the disrupted product by the techniques described above. For example, after completion of culture, the cells collected by centrifugation are suspended in a buffer for cell disruption (20 to 100 mM sodium acetate (pH 5.5), 5 mM EDTA), and disrupted by ultrasonication. The disruption-treated fluid is centrifuged at 10,000 to 15,000 rpm for 10 to 15 minutes to thereby obtain a supernatant. The precipitate after centrifugation can optionally be solubilized with guanidinium chloride, urea, or the like, and then further purified.

The xylanase activity of the obtained polypeptide can be measured by a saccharification test using a xylan-containing biomass (e.g., bagasse) as a substrate. For example, the activity of the purified enzyme can be measured by the method disclosed in Bailey et al., J. Biotech. 23, 1992, pp. 257-270.

6. Process for Producing Xylose/Xylooligosaccharides

The polypeptide having xylanase activity, when contacted with a sample containing xylan (e.g., a biomass resource), decomposes the biomass resource to thereby produce molasses containing xylose and/or oligoxylose. When a biomass resource is used as a xylan-containing sample, molasses can be produced more efficiently by using the above polypeptide in combination with other enzymes, such as cellulase.

The type of xylan-containing sample is not particularly limited, as long as the sample is decomposable by the above polypeptide. Examples of xylan-containing samples include bagasse, wood, bran, wheat straw, rice straw, chaff, soybean meal, soy pulp, coffee grounds, and rice bran.

To produce molasses containing xylose and/or oligoxylose from a xylan-containing sample, a known method can be used. Biomass resources for use may be either dried materials or wet materials. The materials are preferably milled into particles of 100 to 1,000 μm in size beforehand to increase processing efficiency. Milling is performed by using a device such as a ball mill, a vibrational mill, a cutter mill, or a hammer mill. The milled biomass resource is suspended in an aqueous vehicle, and xylanase and cellulase are added thereto, followed by heating with stirring to thereby decompose or saccharize the biomass resource. Moreover, the biomass resource is treated with hot water at 100 to 300° C., preferably 130 to 200° C., for 0.5 to 60 minutes to extract a soluble fraction containing xylan, and xylanase is added to thereby saccharize xylan. The hot-water-treatment residue can be saccharized by adding xylanase and cellulase thereto. The xylanase may be used singly, but is preferably added together with other enzymes, such as cellulase and hemicellulase, to a sample from the standpoint of efficient decomposition of the biomass.

When the polypeptide is contacted with a xylan-containing sample in an aqueous solution, the pH and the temperature of the reaction liquid can be suitably determined as long as the xylanase is not deactivated. Because of the relatively high optimum temperature and excellent temperature stability of xylanase, it is preferable to carry out the reaction at or around the optimum temperature from the standpoint of efficient decomposition of the sample to obtain molasses. For example, the process can be carried out under ordinary pressure, a pH of 3.5 to 8, and a temperature of 5 to 90° C., preferably 15 to 80° C., more preferably 30 to 70° C., even more preferably 30 to 75° C. There is no particular limitation to the amount of the polypeptide to be added, and the amount can be within the range of, for example, 0.01 to 0.5% (w/w).

The molasses containing xylose and/or oligoxylose obtained by the above process may be used unmodified, or may be used as a dry product after removing water. It is also possible to further isomerize or decompose the molasses by a chemical reaction or enzymatic reaction depending on the intended use. The molasses or its fraction can be used, for example, as a starting material for alcohols, such as methanol, ethanol, propanol, isopropanol, butanol, and butanediol, by a fermentation process.

Examples

Examples are shown below; however, the invention disclosed herein is not limited to the Examples.

1. Preparation of Polynucleotide Encoding Modified Xylanase

A polynucleotide (DDBJ Accession No. AB796434) encoding xylanase (xyl10A) was amplified from the chromosomal DNA of *Talaromyces cellulolyticus* CF-2612 strain by the PCR method, and cloned in *Escherichia coli*. In order to delete CBM1 of the above xylanase, a modification was made so that the amino acid codon sequence corresponding to the alanine residue at position 373 of SEQ ID NO: 3 was a stop codon sequence, thereby producing a modified gene that produces a modified xylanase (XylA372), which was 35 amino acid residues shorter than wild-type Xyl10A. Further, in order to delete CBM1 and the linker portion, a modification was similarly made so that the amino acid codon sequence corresponding to the glutamine residue at position 335 of SEQ ID NO: 3 was a stop codon sequence, thereby producing a modified gene that encodes a modified xylanase (XylA334), which was 73 amino acid residues shorter than wild-type Xyl10A.

2. Expression and Purification of Modified Xylanase

A recombinant plasmid in which the polynucleotide encoding modified xylanase XylA372 was functionally connected between the promoter sequence and the terminator sequence of the glucoamylase gene (DDBJ Accession No. AB781686) was produced. Further, a recombinant plasmid in which the polynucleotide encoding modified xylanase XylA334 was functionally connected between the promoter sequence and the terminator sequence of the glucoamylase gene was similarly produced. These plasmids were each heterologously incorporated into the chromosome of a uracil-requiring strain (YP-4 strain) of *Acremonium cellulolyticus* (former name of *Talaromyces cellulolyticus*) obtained according to the process described in the document (J. Ind. Microbiol. Biotechnol. 2013, 40(8): 823-830) using the protoplast-PEG method. Each of the obtained transformants was cultured in a medium containing starch as a carbon source under the control of a glucoamylase promoter. Thus, the modified xylanases were secreted and produced outside the cells.

The cells were removed from the culture medium, and the culture supernatant containing each modified xylanase was subjected to a variety of column chromatographic approaches to purify each modified xylanase. It was confirmed by SDS-polyacrylamide electrophoresis analysis that the purified product was an electrophoretically single protein solution. The wild-type xylanase (Xyl10A) was obtained by culturing a transformant that produces wild-type Xyl10A in a medium containing starch as a carbon source under the control of a glucoamylase promoter reported in the document (Protein. Expr. Purif. 94: 40-45 (2014)), thereby producing the wild-type xylanase upon induction outside the cells. Thereafter, an electrophoretically single enzyme was obtained according to the same document.

3. Comparison of Enzyme Activity Between Modified Xylanase and Wild-Type Xylanase The enzyme activities of modified xylanase XylA372, modified xylanase XylA334, and wild-type xylanase Xyl10A were compared using various xylan substrates. A purified enzyme protein (final concentration: 0.0005 to 0.001 mg/ml) was added to a 50-mM sodium acetate buffer (pH 5.0) containing, as a substrate, a xylan substrate (final concentration: 1%) to initiate the enzyme reaction, and the mixture was kept warm at 45 or 70° C. for 10 minutes. The enzyme activity was calculated by quantifying reducing sugars generated during the reaction, and the relative activity based on the enzyme activity of wild-type xylanase Xyl10A per nmol, which was regarded as 100%, was determined. The following Table 1 shows the results.

TABLE 1

| Substrate | Reaction temperature (° C.) | Relative activity (%) | |
|---|---|---|---|
| | | XylA372 | XylA334 |
| 1% birchwood xylan | 45 | 140 | 130 |
| 1% birchwood xylan | 70 | 190 | 170 |
| 1% wheat arabinoxylan | 45 | 160 | 130 |
| 1% oat-spelt xylan | 45 | 150 | 150 |

As shown in Table 1, when 1% birchwood xylan, 1% wheat arabinoxylan, and 1% oat-spelt xylan were each used as a substrate, the enzyme activities of modified xylanases XylA372 and XylA334 at 45° C. were 1.3 times to 1.6 times higher than the activity of wild-type xylanase Xyl10A. Moreover, when 1% birchwood xylan was used as a substrate, the enzyme activities of modified xylanases XylA372 and XylA334 at 70° C. were 1.7 times to 1.9 times higher than that of the wild-type enzyme.

4. Thermal Stability and pH Stability

Figure 1:
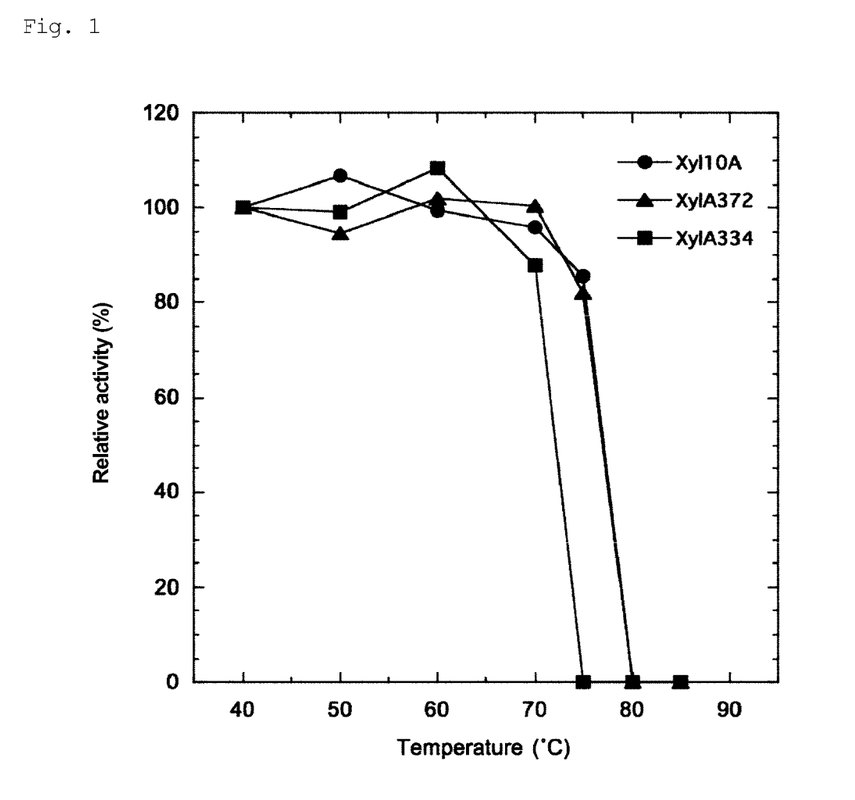
FIG. 1 shows the thermal stability of modified xylanases produced in the Examples.

The wild-type xylanase and the modified xylanases were each kept warm in a 50-mM sodium acetate buffer (pH 5.0) at temperatures of 40 to 80° C. for 10 minutes. After the temperature was returned to room temperature, a xylan substrate suspended in a 50-mM sodium acetate buffer (pH 5.0) was added to the enzyme solution so that the final concentration was 1%, and the enzyme reaction was carried out at 45° C. for 10 minutes. The relative activity based on the activity of each enzyme after heat treatment at 40° C., which was regarded as 100%, was calculated. As a result, it was observed that all the enzymes maintained 85% of enzyme activity at temperatures up to 70° C., and it was confirmed that the modified xylanases maintained heat resistance (FIG. 1). As shown in FIG. 1, the thermal stability of the modified xylanase (XylA334) was slightly lower than that of the wild type and the other modified xylanase (XylA372). This is considered to be attributable to deletion of one residue from the amino acids (20-335) in the catalytic domain of xylanase. Accordingly, if the deleted residue is added (to produce, for example, XylA335 or XylA336), the stability is considered to be close to that of the wild-type xylanase (Xyl10A).

Figure 2:
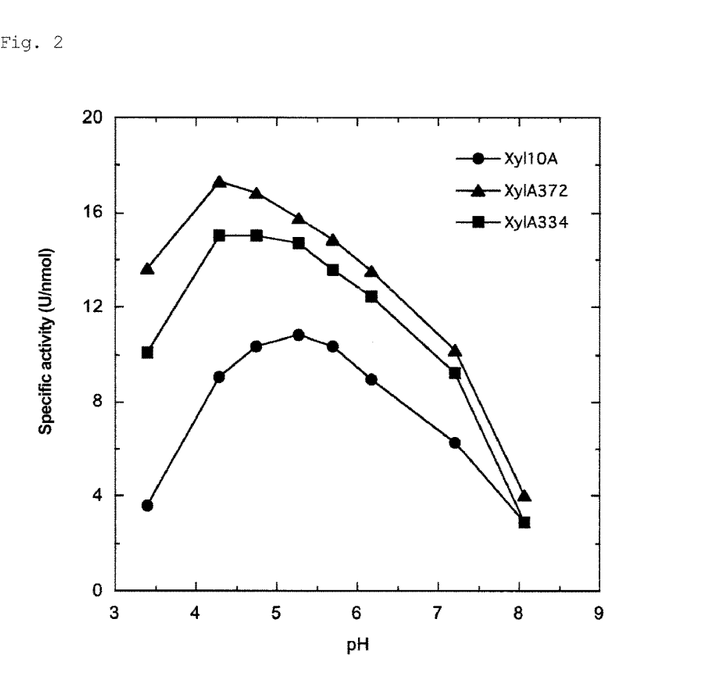
FIG. 2 shows the specific activity of the modified xylanases produced in the Examples at each pH.

The influence of pH on the activity of each enzyme when 1% birchwood xylan was used as a substrate was compared. The buffer used was a McIlvain buffer (pH: 3.4 to 8.0). The enzyme reaction was carried out at 45° C. for 10 minutes, and the specific activity (U/nmol) of each enzyme at each pH was calculated based on the produced reducing sugars. The reaction optimal pH of the wild-type enzyme was around 5, and that of the modified enzymes was around 4.5. Further, it was found that modified xylanases XylA372 and XylA334 showed stable enzyme activity on the acidic side. For example, the specific activities of modified xylanases XylA372 and XylA334 at a pH of 3.4 were, respectively, 3.8 times and 2.8 times higher than the activity of wild-type Xyl10A (FIG. 2). The activities of modified xylanases XylA372 and XylA334 at a pH of 7.0 were, respectively, 1.6 times and 1.5 times higher than the specific activity of wild-type Xyl10A (FIG. 2). That is, it was confirmed that both modified xylanases maintained the heat resistance of the wild-type enzyme, and that the xylan hydrolysis activity was more highly improved than the wild type in various temperature and pH environments.

5. Consideration of the Structure of Modified Xylanase

From a structural viewpoint, the amino acid sequence of wild-type xylanase Xyl10A is divided into a signal peptide sequence (amino acid residue Nos. 1-19), a catalytic domain (amino acid residue Nos. 20-335), a linker sequence (amino acid residue Nos. 336-372), and CBM1 (amino acid residue Nos. 373-407) (FIG. 3). Because the activity of XylA372, in which CBM1 was completely deleted, was higher than that of the wild type, the increase in enzyme activity is considered to be attributable to the deletion of CBM1. It has been reported that the deletion of CBM1 in xylanase and hemicellulase, both of which have CBM1, does not contribute to the improvement of enzyme activity.

An increase in the activity of xylanase is expected by making a modification so that the structure of CBM1 is not formed. For example, the functional structure of CBM1 is strengthened in such a manner that the cysteine residues at positions 379 and 396 and the cysteine residues at positions 390 and 406 in the amino acid sequence of SEQ ID NO: 3 each form a disulfide bond. Therefore, it is assumed that deletion from the carboxy terminus to the cysteine residue at position 396 in wild-type xylanase Xyl10A makes the formation of two disulfide bonds impossible, thereby losing the structure peculiar to CBM1. Such modified enzymes are also expected to exhibit the effect of improving enzyme activity, as with the present invention (FIG. 3). That is, an increase in enzyme activity is also expected for modified xylanases in which amino acid residues from the carboxy terminus to at least the cysteine residue at position 396 in wild-type xylanase Xyl10A are deleted, and in which amino acids at positions 397 to 335 are sequentially deleted (FIG. 3). Due to the deletion of CBM1, the affinity of xylanase to cellulose is lost. Enzymes in which a sequence that forms a useful domain structure (e.g., cellulose-binding CBM2a, CBM3, CBM5, CBM10, etc., and xylan-binding CBM2b, CBM6, CBM9, and CBM22) is attached to the C-terminus or N-terminus of modified enzymes so as to supplement the affinity function are expected to become biomass-binding xylanases that maintain the activity of the modified enzymes.

A modified xylanase can be prepared by using the genomic DNA sequence represented by SEQ ID NO: 6, and can also be prepared by using a cDNA sequence (e.g., SEQ ID NO: 4 or 5) obtained from the transfer RNA derived from the xyl10A gene.

It is also possible to obtain an enzyme in which amino acid residues that do not contribute to heat resistance or enzyme activity in the amino acid sequence of wild-type xylanase Xyl10A are substituted with other amino acids, or a further modified xylanase with substitution with amino acid residues that have the effect of further increasing heat resistance or enzyme activity. Multiple amino acid residues can be added to the N- or C-terminus of the modified xylanase within a range in which the activity is not affected. For example, an amino acid tag for protein purification can be attached to the terminus of the modified xylanase.

The invention claimed is:

1. An isolated polypeptide comprising an amino acid sequence having at least 90% identity to the amino acid sequence of SEQ ID NO: 1, wherein 12 or more and 73 or fewer consecutive amino acid residues from the C-terminus of the amino acid sequence of SEQ ID NO: 1 are deleted, and wherein the polypeptide has xylanase activity.

2. The isolated polypeptide according to claim 1, wherein the amino acid sequence has at least 95% identity to the amino acid sequence of SEQ ID NO: 1.

3. The isolated polypeptide according to claim 1, wherein the polypeptide has glutamic acid residues at positions corresponding to position 129 and position 236 of SEQ ID NO: 1.

4. A polynucleotide encoding the isolated polypeptide according to claim 1.

5. An expression vector incorporating the polynucleotide according to claim 4.

6. A host cell containing the polynucleotide according to claim 4.

7. A process for producing a polypeptide, the process comprising:
culturing the host cell according to claim 6, and
collecting the polypeptide contained in the host cell.

8. The isolated polypeptide according to claim 2, wherein the isolated polypeptide has:
glutamic acid residues at positions corresponding to position 129 and position 236 of SEQ ID NO: 1;
a lysine residue at a position corresponding to position 47 of SEQ ID NO: 1;
histidine residues at positions corresponding to position 80 and position 206 of SEQ ID NO: 1;
tryptophan residues at positions corresponding to position 84, position 276, and position 284 of SEQ ID NO: 1; and
a glutamine residue at a position corresponding to position 204 of SEQ ID NO: 1.

9. A polynucleotide encoding the isolated polypeptide according to claim 2.

10. A polynucleotide encoding the isolated polypeptide according to claim 3.

11. A polynucleotide encoding the isolated polypeptide according to claim 8.

12. An expression vector incorporating the polynucleotide according to claim 9.

13. An expression vector incorporating the polynucleotide according to claim 10.

14. An expression vector incorporating the polynucleotide according to claim 11.

15. A host cell containing the polynucleotide according to claim 9.

16. A host cell containing the polynucleotide according to claim 10.

17. A host cell containing the polynucleotide according to claim 11.

18. A host cell containing the expression vector according to claim 5.

19. A host cell containing the expression vector according to claim 12.

20. A host cell containing the expression vector according to claim 13.

21. A host cell containing the expression vector according to claim 14.

22. A process for producing a polypeptide, the process comprising:
culturing the host cell according to claim 18, and
collecting the polypeptide contained in the host cell.

* * * * *

SEQUENCE LISTING

```
<160> NUMBER OF SEQ ID NOS: 7

<210> SEQ ID NO 1
<211> LENGTH: 388
<212> TYPE: PRT
<213> ORGANISM: Talaromyces cellulolyticus

<400> SEQUENCE: 1

Gln Leu Asn Thr Ala Ala Lys Ala Ala Gly Leu Leu Tyr Phe Gly Thr
1               5                   10                  15

Ala Val Asp Asn Pro Asp Leu Ser Asp Ser Lys Tyr Ile Ala Asn Leu
            20                  25                  30

Glu Thr Ala Asp Phe Gly Gln Ile Thr Pro Ala Asn Ala Met Lys Trp
        35                  40                  45

Gln Pro Thr Glu Pro Ser Gln Gly Ser Tyr Thr Phe Thr Gln Gly Asp
    50                  55                  60

Gln Ile Ala Ser Leu Ala Lys Ser Asn Asn Asp Tyr Leu Arg Cys His
65                  70                  75                  80

Asn Leu Val Trp Tyr Asn Gln Leu Pro Ser Tyr Ile Thr Ser Gly Ser
                85                  90                  95

Trp Thr Asn Ala Thr Leu Ile Ala Ala Leu Lys Glu His Ile Asn Gly
            100                 105                 110

Val Val Thr His Tyr Lys Gly Gln Cys Tyr Ala Trp Asp Val Val Asn
        115                 120                 125

Glu Ala Leu Asn Glu Asp Gly Thr Tyr Arg Gln Asn Val Phe Tyr Gln
    130                 135                 140

Tyr Ile Gly Glu Ala Tyr Ile Pro Ile Ala Phe Ala Ala Ala Ala Ala
145                 150                 155                 160

Ala Asp Pro Asn Ala Lys Leu Tyr Tyr Asn Asp Tyr Asn Ile Glu Tyr
                165                 170                 175

Ala Gly Ser Lys Ala Thr Gly Ala Gln Arg Ile Val Lys Leu Ile Gln
            180                 185                 190

Ala Ala Gly Gly Arg Ile Asp Gly Val Gly Leu Gln Ser His Phe Ile
        195                 200                 205

Val Gly Gln Thr Pro Ser Leu Ala Thr Gln Lys Ala Asn Met Ala Ala
    210                 215                 220

Phe Thr Ala Leu Gly Val Asp Val Ala Ile Thr Glu Leu Asp Ile Arg
225                 230                 235                 240

Met Thr Leu Pro Asp Thr Ser Ala Leu Gln Thr Gln Ser Thr Asp
                245                 250                 255

Tyr Gln Thr Thr Thr Thr Ala Cys Val Gln Thr Lys Gly Cys Val Gly
            260                 265                 270

Ile Thr Leu Trp Asp Tyr Thr Asp Lys Tyr Ser Trp Val Pro Gly Thr
        275                 280                 285

Phe Ser Gly Gln Gly Asp Ala Cys Pro Trp Asp Ser Asn Tyr Asn Lys
    290                 295                 300

Lys Pro Ala Tyr Tyr Gly Ile Leu Ala Gly Leu Gln Ser Gly Thr Gly
305                 310                 315                 320

Ser Ser Ser Ser Thr Ser Ser Thr Leu Thr Thr Thr Thr Pro
                325                 330                 335

Thr Thr Ala Ser Ser Thr Thr Ser Thr Ser Thr Ser Ala Thr Ser
            340                 345                 350
```

-continued

Gly Ala Ala His Trp Gly Gln Cys Gly Gly Ile Gly Trp Ser Gly Pro
            355                 360                 365

Thr Ile Cys Val Ser Pro Tyr Thr Cys Gln Val Leu Asn Pro Tyr Tyr
        370                 375                 380

Ser Gln Cys Leu
385

<210> SEQ ID NO 2
<211> LENGTH: 19
<212> TYPE: PRT
<213> ORGANISM: Talaromyces cellylolyticus

<400> SEQUENCE: 2

Met Thr Leu Val Lys Ala Ile Leu Leu Ala Leu Ala Met Gly His Val
1               5                   10                  15

Ala Gln Ala

<210> SEQ ID NO 3
<211> LENGTH: 407
<212> TYPE: PRT
<213> ORGANISM: Talaromyces cellylolyticus

<400> SEQUENCE: 3

Met Thr Leu Val Lys Ala Ile Leu Leu Ala Leu Ala Met Gly His Val
1               5                   10                  15

Ala Gln Ala Gln Leu Asn Thr Ala Ala Lys Ala Ala Gly Leu Leu Tyr
            20                  25                  30

Phe Gly Thr Ala Val Asp Asn Pro Asp Leu Ser Asp Ser Lys Tyr Ile
        35                  40                  45

Ala Asn Leu Glu Thr Ala Asp Phe Gly Gln Ile Thr Pro Ala Asn Ala
    50                  55                  60

Met Lys Trp Gln Pro Thr Glu Pro Ser Gln Gly Ser Tyr Thr Phe Thr
65              70                  75                  80

Gln Gly Asp Gln Ile Ala Ser Leu Ala Lys Ser Asn Asn Asp Tyr Leu
            85                  90                  95

Arg Cys His Asn Leu Val Trp Tyr Asn Gln Leu Pro Ser Tyr Ile Thr
        100                 105                 110

Ser Gly Ser Trp Thr Asn Ala Thr Leu Ile Ala Ala Leu Lys Glu His
    115                 120                 125

Ile Asn Gly Val Val Thr His Tyr Lys Gly Gln Cys Tyr Ala Trp Asp
130                 135                 140

Val Val Asn Glu Ala Leu Asn Glu Asp Gly Thr Tyr Arg Gln Asn Val
145                 150                 155                 160

Phe Tyr Gln Tyr Ile Gly Glu Ala Tyr Ile Pro Ile Ala Phe Ala Ala
            165                 170                 175

Ala Ala Ala Ala Asp Pro Asn Ala Lys Leu Tyr Tyr Asn Asp Tyr Asn
        180                 185                 190

Ile Glu Tyr Ala Gly Ser Lys Ala Thr Gly Ala Gln Arg Ile Val Lys
    195                 200                 205

Leu Ile Gln Ala Ala Gly Gly Arg Ile Asp Gly Val Gly Leu Gln Ser
210                 215                 220

His Phe Ile Val Gly Gln Thr Pro Ser Leu Ala Thr Gln Lys Ala Asn
225                 230                 235                 240

Met Ala Ala Phe Thr Ala Leu Gly Val Asp Val Ala Ile Thr Glu Leu
            245                 250                 255

Asp Ile Arg Met Thr Leu Pro Asp Thr Ser Ala Leu Gln Thr Gln Gln

-continued

```
            260                 265                 270

Ser Thr Asp Tyr Gln Thr Thr Thr Thr Ala Cys Val Gln Thr Lys Gly
        275                 280                 285

Cys Val Gly Ile Thr Leu Trp Asp Tyr Thr Asp Lys Tyr Ser Trp Val
    290                 295                 300

Pro Gly Thr Phe Ser Gly Gln Gly Asp Ala Cys Pro Trp Asp Ser Asn
305                 310                 315                 320

Tyr Asn Lys Lys Pro Ala Tyr Tyr Gly Ile Leu Ala Gly Leu Gln Ser
                325                 330                 335

Gly Thr Gly Ser Ser Ser Ser Thr Ser Ser Thr Thr Leu Thr Thr Thr
            340                 345                 350

Thr Thr Pro Thr Thr Ala Ser Ser Thr Thr Ser Thr Thr Ser Thr Ser
        355                 360                 365

Ala Thr Ser Gly Ala Ala His Trp Gly Gln Cys Gly Gly Ile Gly Trp
    370                 375                 380

Ser Gly Pro Thr Ile Cys Val Ser Pro Tyr Thr Cys Gln Val Leu Asn
385                 390                 395                 400

Pro Tyr Tyr Ser Gln Cys Leu
                405

<210> SEQ ID NO 4
<211> LENGTH: 1167
<212> TYPE: DNA
<213> ORGANISM: Talaromyces cellylolyticus
<400> SEQUENCE: 4
caattgaaca cggccgcaaa agcagctggt ctattgtact ttggtactgc ggttgacaat     60
ccagacttga gcgactccaa atatattgca aaccttgaga ctgcggattt cggtcagatc    120
acgccagcaa atgcaatgaa atggcaaccc accgagccgt ctcaaggctc ctatactttc    180
actcagggtg accagatcgc gagcctggcc aagtctaata atgactactt gagatgccat    240
aatctggtct ggtacaacca gttgccgtca tacattactt cgggttcatg gacaaacgca    300
acccttattg ctgccttgaa ggagcatatc aatggagttg tcacgcatta caagggacaa    360
tgctacgcgt gggatgttgt aaacgaagcc ttgaacgaag acggcaccta tcgtcaaaat    420
gttttctacc aatatatagg cgaggcatac attccaattg cgtttgctgc cgctgcagcc    480
gcggacccta atgccaagtt gtactacaac gactacaaca tcgaatacgc tgggtcaaag    540
gcaactggtg ctcagcgcat tgtaaaatta attcaagctg ctggtggtcg tatcgatggc    600
gtgggtcttc agtctcactt cattgtggga caaaccccta gtcttgccac tcagaaagca    660
aacatggctg cttttactgc tctcggtgtt gatgttgcca ttactgagct tgacattcgt    720
atgactctcc cggataccag cgctcttcaa actcagcagt ccaccgacta ccagaccacc    780
actactgcct gcgtccagac taaaggctgt gttggtatca cgctatggga ttacacagac    840
aagtactcat gggttcccgg taccttctct ggccagggtg atgcttgtcc atgggactca    900
aactacaaca agaagccggc atactatggt atccttgctg gcttacaatc tggcactggt    960
tcttcatcgt caacttctag caccacccta acaaccacca caacacccac taccgcttca   1020
agtactacgt caacgactag cacaagcgct acctcaggtg ctgcacactg ggacaatgc   1080
ggaggcattg gctggtctgg tcctaccatt tgtgtttcgc cctacacttg tcaagtgttg   1140
aacccatact actcccaatg tttgtaa                                        1167

<210> SEQ ID NO 5
```

<211> LENGTH: 1224
<212> TYPE: DNA
<213> ORGANISM: Talaromyces cellulolyticus

<400> SEQUENCE: 5

| | | | | | |
|---|---|---|---|---|---|
| atgactctag | taaaggctat | tcttttagcg | cttgctatgg | gccacgttgc | ccaggcccaa | 60 |
| ttgaacacgg | ccgcaaaagc | agctggtcta | ttgtactttg | gtactgcggt | tgacaatcca | 120 |
| gacttgagcg | actccaaata | tattgcaaac | cttgagactg | cggatttcgg | tcagatcacg | 180 |
| ccagcaaatg | caatgaaatg | caacccacc | gagccgtctc | aaggctccta | tactttcact | 240 |
| cagggtgacc | agatcgcgag | cctggccaag | tctaataatg | actacttgag | atgccataat | 300 |
| ctggtctggt | acaaccagtt | gccgtcatac | attacttcgg | gttcatggac | aaacgcaacc | 360 |
| cttattgctg | ccttgaagga | gcatatcaat | ggagttgtca | cgcattacaa | gggacaatgc | 420 |
| tacgcgtggg | atgttgtaaa | cgaagccttg | aacgaagacg | gcacctatcg | tcaaaatgtt | 480 |
| ttctaccaat | atataggcga | ggcatacatt | ccaattgcgt | tgctgccgc | tgcagccgcg | 540 |
| gaccctaatg | ccaagttgta | ctacaacgac | tacaacatca | atacgctgg | gtcaaaggca | 600 |
| actggtgctc | agcgcattgt | aaaattaatt | caagctgctg | gtggtcgtat | cgatggcgtg | 660 |
| ggtcttcagt | ctcacttcat | tgtgggacaa | accctagtc | ttgccactca | gaaagcaaac | 720 |
| atggctgctt | ttactgctct | cggtgttgat | gttgccatta | ctgagcttga | cattcgtatg | 780 |
| actctcccgg | ataccagcgc | tcttcaaact | cagcagtcca | ccgactacca | gaccaccact | 840 |
| actgcctgcg | tccagactaa | aggctgtgtt | ggtatcacgc | tatgggatta | cacagacaag | 900 |
| tactcatggg | ttcccggtac | cttctctggc | cagggtgatg | cttgtccatg | ggactcaaac | 960 |
| tacaacaaga | gccggcata | ctatggtatc | cttgctggct | acaatctgg | cactggttct | 1020 |
| tcatcgtcaa | cttctagcac | caccctaaca | accaccacaa | cacccactac | cgcttcaagt | 1080 |
| actacgtcaa | cgactagcac | aagcgctacc | tcaggtgctg | cacactgggg | acaatgcgga | 1140 |
| ggcattggct | ggtctggtcc | taccatttgt | gtttcgccct | acacttgtca | agtgttgaac | 1200 |
| ccatactact | cccaatgttt | gtaa | | | | 1224 |

<210> SEQ ID NO 6
<211> LENGTH: 1445
<212> TYPE: DNA
<213> ORGANISM: Talaromyces cellulolyticus

<400> SEQUENCE: 6

| | | | | | |
|---|---|---|---|---|---|
| atgactctag | taaaggctat | tcttttagcg | cttgctatgg | gccacgttgc | ccaggcccaa | 60 |
| ttgaacacgg | ccgcaaaagc | agctggtcta | ttgtactttg | gtactgcggt | tgacaatcca | 120 |
| gacttgagcg | actccaaata | tattgcaaac | cttgagactg | cggatttcgg | tcagatcacg | 180 |
| ccagcaaatg | caatgaaagt | cagtggccaa | acctcactac | tgtatacaac | cagctaagtg | 240 |
| atgacaattt | agtggcaacc | caccgagccg | tctcaaggct | cctatacttt | cactcagggt | 300 |
| gaccagatcg | cgagcctggc | caagtctaat | aatgactact | tgagatgcca | taatctggtc | 360 |
| tggtacaacc | agttgccgtc | atacagtaag | caagcatacg | acctccatga | attgtcatcc | 420 |
| aacatacacg | atagcaagct | gatacggtat | ctgtctagtt | acttcgggtt | catggacaaa | 480 |
| cgcaacccct | tattgctgcc | tgaaggagca | tatcaatgga | gttgtcacgc | attacaaggg | 540 |
| acaatgctac | gcgtgggatg | ttgtaaacga | aggtatgcga | tattatatac | aggccctttc | 600 |
| tctgcatcct | tacatctttt | ttatctccat | cctacgtaat | catgtcgagc | taagtgaagt | 660 |
| atctagcctt | gaacgaagac | ggcacctatc | gtcaaaatgt | tttctaccaa | tatataggcg | 720 |

```
aggcatacat tccaattgcg tttgctgccg ctgcagccgc ggaccctaat gccaagttgt    780
actacaacga ctacaacatc gaatacgctg ggtcaaaggc aactggtgct cagcgcattg    840
taaaattaat tcaagctgct ggtggtcgta tcgatggcgt gggtcttcag tctcacttca    900
ttgtgggaca aaccccctagt cttgccactc agaaagcaaa catggctgct tttactgctc    960
tcggtgttga tgttgccatt actgagcttg acattcgtat gactctcccg gataccagcg   1020
ctcttcaaac tcagcagtcc accgactacc agaccaccac tactgcctgc gtccagacta   1080
aaggctgtgt tggtatcacg ctatgggatt acacagacaa gtactcatgg gttcccggta   1140
ccttctctgg ccagggtgat gcttgtccat gggactcaaa ctacaacaag aagccggcat   1200
actatggtat ccttgctggc ttacaatctg gcactggttc ttcatcgtca acttctagca   1260
ccaccctaac aaccaccaca acacccacta ccgcttcaag tactacgtca acgactagca   1320
caagcgctac ctcaggtgct gcacactggg acaatgcgg aggcattggc tggtctggtc   1380
ctaccatttg tgtttcgccc tacacttgtc aagtgttgaa cccatactac tcccaatgtt   1440
tgtaa                                                                1445
```

<210> SEQ ID NO 7
<211> LENGTH: 407
<212> TYPE: PRT
<213> ORGANISM: Penicillium funiculosum

<400> SEQUENCE: 7

```
Met Thr Leu Val Lys Ser Ile Leu Ala Leu Ala Ala Gly His Val
1               5                   10                  15

Ala Gln Ala Gln Leu Asn Thr Ala Ala Lys Ala Gly Leu Leu Tyr
                20                  25                  30

Phe Gly Thr Ala Val Asp Asn Pro Asp Leu Ser Asp Ser Lys Tyr Leu
            35                  40                  45

Val Asn Leu Glu Thr Ala Asp Phe Gly Gln Ile Thr Pro Ala Asn Ala
        50                  55                  60

Met Lys Trp Gln Pro Thr Glu Pro Ser Gln Gly Ser Tyr Thr Phe Thr
65                  70                  75                  80

Gln Gly Asp Gln Ile Ala Ser Leu Ala Lys Ser Asn Asn Asp Tyr Leu
                85                  90                  95

Arg Cys His Asn Leu Val Trp Tyr Asn Gln Leu Pro Ser Tyr Ile Thr
            100                 105                 110

Ser Gly Ser Trp Thr Asn Ala Thr Leu Ile Ala Ala Leu Lys Glu His
        115                 120                 125

Ile Asn Gly Val Val Thr His Tyr Lys Gly Gln Cys Tyr Ala Trp Asp
    130                 135                 140

Val Val Asn Glu Ala Leu Asn Glu Asp Gly Thr Tyr Arg Gln Asn Val
145                 150                 155                 160

Phe Tyr Gln His Ile Gly Glu Ala Tyr Ile Pro Ile Ala Phe Ala Ala
                165                 170                 175

Ala Ala Ala Ala Asp Pro Asn Ala Lys Leu Tyr Tyr Asn Asp Tyr Asn
            180                 185                 190

Ile Glu Tyr Ala Gly Ala Lys Ala Thr Gly Ala Gln Gly Ile Val Lys
        195                 200                 205

Leu Ile Gln Ala Ala Gly Gly Arg Ile Asp Gly Val Gly Leu Gln Ser
    210                 215                 220

His Phe Ile Val Gly Gln Thr Pro Ser Leu Ala Thr Gln Lys Ala Asn
225                 230                 235                 240
```

-continued

```
Met Ala Ala Phe Thr Ala Leu Gly Val Asp Val Ala Ile Thr Glu Leu
            245                 250                 255

Asp Ile Arg Met Thr Leu Pro Asp Thr Ser Ala Leu Gln Thr Gln Gln
            260                 265                 270

Ser Thr Asp Tyr Gln Thr Thr Thr Ala Cys Val Gln Thr Lys Gly
        275                 280                 285

Cys Val Gly Ile Thr Leu Trp Asp Tyr Thr Asp Lys Tyr Ser Trp Val
        290                 295                 300

Pro Gly Thr Phe Ser Gly Gln Gly Asp Ala Cys Pro Trp Asp Ser Asn
305                 310                 315                 320

Tyr Asn Lys Lys Pro Ala Tyr Tyr Gly Ile Leu Ala Gly Leu Gln Ser
                325                 330                 335

Gly Ser Gly Ser Ser Ser Ser Thr Ser Ser Thr Thr Leu Ile Thr Thr
            340                 345                 350

Thr Thr Pro Thr Ala Ser Ser Ser Thr Thr Ser Ala Thr Thr Thr Ser
        355                 360                 365

Ala Thr Ser Gly Ala Ala His Trp Gly Gln Cys Gly Gly Ile Gly Trp
    370                 375                 380

Ser Gly Pro Thr Ile Cys Val Ser Pro Tyr Thr Cys Gln Val Leu Asn
385                 390                 395                 400

Pro Tyr Tyr Ser Gln Cys Leu
                405
```